US012571762B2

(12) United States Patent
Ranjan et al.

(10) Patent No.: US 12,571,762 B2
(45) Date of Patent: Mar. 10, 2026

(54) DURABLE ELECTROCHEMICAL GAS DETECTION DEVICE

(71) Applicant: CARRIER CORPORATION, Palm Beach Gardens, FL (US)

(72) Inventors: Rajiv Ranjan, South Windsor, CT (US); Marcin Piech, East Hampton, CT (US)

(73) Assignee: KIDDE FIRE PROTECTION, LLC, Bradenton, FL (US)

( * ) Notice: Subject to any disclaimer, the term of this patent is extended or adjusted under 35 U.S.C. 154(b) by 493 days.

(21) Appl. No.: 17/706,780

(22) Filed: Mar. 29, 2022

(65) Prior Publication Data

US 2022/0317085 A1     Oct. 6, 2022

Related U.S. Application Data

(60) Provisional application No. 63/169,353, filed on Apr. 1, 2021.

(51) Int. Cl.
 *G01N 33/00*          (2006.01)
 *G01N 27/407*         (2006.01)

(52) U.S. Cl.
 CPC ..... *G01N 27/4077* (2013.01); *G01N 27/4071* (2013.01); *G01N 33/0027* (2013.01)

(58) Field of Classification Search
 CPC ............... G01N 27/40; G01N 27/4077; G01N 27/4071; G01N 33/0027; G01N 33/0009; G01N 27/12; G01N 27/404; G01N 27/126; G01N 27/30
 See application file for complete search history.

(56) References Cited

U.S. PATENT DOCUMENTS

| | | | | |
|---|---|---|---|---|
| 3,708,412 A | * | 1/1973 | Lofgren | ................. G01N 27/40 |
| | | | | 204/415 |
| 4,100,048 A | | 7/1978 | Pompei et al. | |
| 4,810,352 A | | 3/1989 | Bone et al. | |
| 4,975,175 A | | 12/1990 | Karube et al. | |
| 5,004,532 A | | 4/1991 | Hale | |
| 5,387,329 A | | 2/1995 | Foos et al. | |

(Continued)

FOREIGN PATENT DOCUMENTS

| | | |
|---|---|---|
| CN | 201788166 U | 4/2011 |
| CN | 102192931 B | 4/2013 |

(Continued)

OTHER PUBLICATIONS

Behzad Fotovvati et al., On Coating Techniques for Surface Protection: A Review, 2019, Journal of Manufacturing and Materials Processing, 3(1), 28 (Year: 2019).*

(Continued)

*Primary Examiner* — Luan V Van
*Assistant Examiner* — Kaylee Tseng
(74) *Attorney, Agent, or Firm* — CANTOR COLBURN LLP

(57)          ABSTRACT

A gas detection device includes a housing, a top disk, an electrochemical sensor, a gasket, and an electrically resistive material, the top disk, electrochemical sensor, gasket and electrically resistive material are located in the housing and the electrically resistive material is located between the housing and the gasket, between the gasket and the top disk, or dispersed through the gasket.

8 Claims, 4 Drawing Sheets

(56) References Cited

U.S. PATENT DOCUMENTS

| | | | |
|---|---|---|---|
| 5,573,648 | A | 11/1996 | Shen et al. |
| 5,582,698 | A | 12/1996 | Flaherty et al. |
| 5,700,360 | A | 12/1997 | Chan et al. |
| 5,851,369 | A * | 12/1998 | Cai ..................... G01N 27/407 |
| | | | 205/784.5 |
| 6,478,950 | B1 | 11/2002 | Peat et al. |
| 7,608,177 | B2 * | 10/2009 | Nauber ............... G01N 27/404 |
| | | | 204/411 |
| 7,767,068 | B2 | 8/2010 | Lauks et al. |
| 9,109,700 | B2 | 8/2015 | Scholz |
| 10,908,117 | B2 | 2/2021 | Bhat et al. |
| 2003/0145644 | A1 * | 8/2003 | Rabbett .............. G01N 33/0006 |
| | | | 73/23.31 |
| 2004/0134780 | A1 * | 7/2004 | Inoue ................. G01N 27/4071 |
| | | | 204/426 |
| 2013/0062223 | A1 * | 3/2013 | Rabbett .............. G01N 27/4045 |
| | | | 29/595 |
| 2013/0175168 | A1 * | 7/2013 | Nemes ................. C08G 61/123 |
| | | | 204/415 |
| 2013/0337218 | A1 * | 12/2013 | Liu ................... B29C 66/91411 |
| | | | 156/110.1 |
| 2019/0227026 | A1 * | 7/2019 | Bhat .................... G01N 27/404 |
| 2020/0209186 | A1 * | 7/2020 | Liu ................... G01N 27/4045 |

FOREIGN PATENT DOCUMENTS

| | | | | |
|---|---|---|---|---|
| DE | 10361749 | A1 | | 7/2005 |
| DE | 102013212366 | A1 | | 12/2014 |
| JP | 2002350393 | A | * | 12/2002 |
| JP | 2003303596 | A | | 10/2003 |
| JP | 2016205530 | A | * | 12/2016 |
| WO | 9102970 | A1 | | 3/1991 |
| WO | WO-0010216 | A1 | * | 2/2000 .......... H01M 8/0271 |

OTHER PUBLICATIONS

Durlon 8500 Aramid/Inorganic with NBR Rubber Binder Compressed Non-Asbestos Gasket Material, 2020, Durlon Sealing Solutions (Year: 2020).*

James Shackelford et al., CRC Materials Science and Engineering Handbook, 2015, Taylor & Francis, 4th Edition, pp. 510-513 (Year: 2015).*

OpenStax, College Physics—20.3 Resistance and Resistivity, 2016, OpenStax CNX, pp. 736-745 (Year: 2016).*

Victrex, "Victrex PEEK polymer 450G," 2024, Victrex Manufacturing Limited (Year: 2024).*

European Search Report for Application No. 22165253.0, Issued Jul. 22, 2022, 8 Pages.

* cited by examiner

DURABLE ELECTROCHEMICAL GAS DETECTION DEVICE

CROSS-REFERENCE TO RELATED APPLICATIONS

This application claims the benefit of U.S. provisional patent application No. 63/169,353, filed Apr. 1, 2021, the entire contents of which is incorporated herein by reference in its entirety.

BACKGROUND

Exemplary embodiments pertain to the art of electrochemical sensors for gaseous compounds.

Many electrochemical sensors utilize a membrane electrode assembly (MEA) to detect specific compounds. The lifetime and performance of electrochemical sensors for gaseous compounds may be limited by the durability of the electrochemical sensor. The durability of the electrochemical sensor can be impacted by the degradation of gasket materials. There is therefore a need for an improved gas detection device.

BRIEF DESCRIPTION

Disclosed is a gas detection device including a housing, a top disk, an electrochemical sensor, a gasket, and an electrically resistive material, wherein the top disk, electrochemical sensor, gasket and electrically resistive material are located in the housing and the electrically resistive material is located between the housing and the gasket.

In addition to one or more of the features described above, or as an alternative to any of the foregoing embodiments, the electrochemical sensor comprises a membrane electrode assembly.

In addition to one or more of the features described above, or as an alternative to any of the foregoing embodiments, the electrically resistive material is in contact with the housing, the gasket, or the housing and the gasket.

In addition to one or more of the features described above, or as an alternative to any of the foregoing embodiments, the electrically resistive material has a thickness of 2 to 5000 micrometers.

In addition to one or more of the features described above, or as an alternative to any of the foregoing embodiments, the electrically resistive material has a thickness of 10 to 1000 micrometers.

In addition to one or more of the features described above, or as an alternative to any of the foregoing embodiments, the electrically resistive material has an electrical resistance greater than or equal to 100,000 ohms.

In addition to one or more of the features described above, or as an alternative to any of the foregoing embodiments, the electrically resistive material comprises a paint, a film, or an anodization layer.

Also disclosed is a gas detection device comprising a housing, a top disk, an electrochemical sensor, a gasket, and an electrically resistive material wherein the top disk, electrochemical sensor, gasket and electrically resistive material are located in the housing and the electrically resistive material is located between the top disk and the gasket.

In addition to one or more of the features described above, or as an alternative to any of the foregoing embodiments, the electrochemical sensor comprises a membrane electrode assembly.

In addition to one or more of the features described above, or as an alternative to any of the foregoing embodiments, the electrically resistive material is in contact with the top disk, the gasket or both the top disk and the gasket.

In addition to one or more of the features described above, or as an alternative to any of the foregoing embodiments, the electrically resistive material has a thickness of 10 to 5000 micrometers.

In addition to one or more of the features described above, or as an alternative to any of the foregoing embodiments, the electrically resistive material comprises a paint, a film, or an anodization layer.

In addition to one or more of the features described above, or as an alternative to any of the foregoing embodiments, the electrically resistive material has an electrical resistance greater than or equal to 100,000 ohms.

Also disclosed is a gas detection device comprising a housing, a top disk, an electrochemical sensor, and a composite gasket, wherein the composite gasket comprises an electrically resistive material on an exterior surface and a material different from the electrically resistive material on an interior surface of the composite gasket, an electrically resistive material located between two layers of material different from the electrically resistive material, or an electrically resistive material dispersed in a material different from the electrically resistive material.

In addition to one or more of the features described above, or as an alternative to any of the foregoing embodiments, the electrochemical sensor comprises a membrane electrode assembly.

In addition to one or more of the features described above, or as an alternative to any of the foregoing embodiments, the gasket exterior surface comprising the electrically resistive material is located adjacent to the housing.

In addition to one or more of the features described above, or as an alternative to any of the foregoing embodiments, the gasket exterior surface comprising the electrically resistive material is located adjacent to the top disk.

In addition to one or more of the features described above, or as an alternative to any of the foregoing embodiments, the electrically resistive material has a thickness of 10 to 5000 micrometers.

In addition to one or more of the features described above, or as an alternative to any of the foregoing embodiments, the electrically resistive material has an electrical resistance greater than or equal to 100,000 ohms.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

Electrochemical sensor performance and durability relies, at least in part, on a durable gasket material with high electrical resistivity (little or no electrical conductivity). Currently employed gasket materials, such as natural rubber, butyl rubber and carbon filled rubber, may degrade over time and result in current bypass. Current bypass causes a lower sensor signal, decreased sensitivity, and shortened sensor life. To address this problem, the gas detection device described herein includes an electrically resistive material located between the gasket and the sensor housing or between the gasket and the top disk. The electrically resistive material provides a barrier to current bypass that may occur as a result of gasket degradation. By providing an extra layer of resistive material the durability of the gas detection device is improved and the lifetime of the device is extended.

Figure 1:
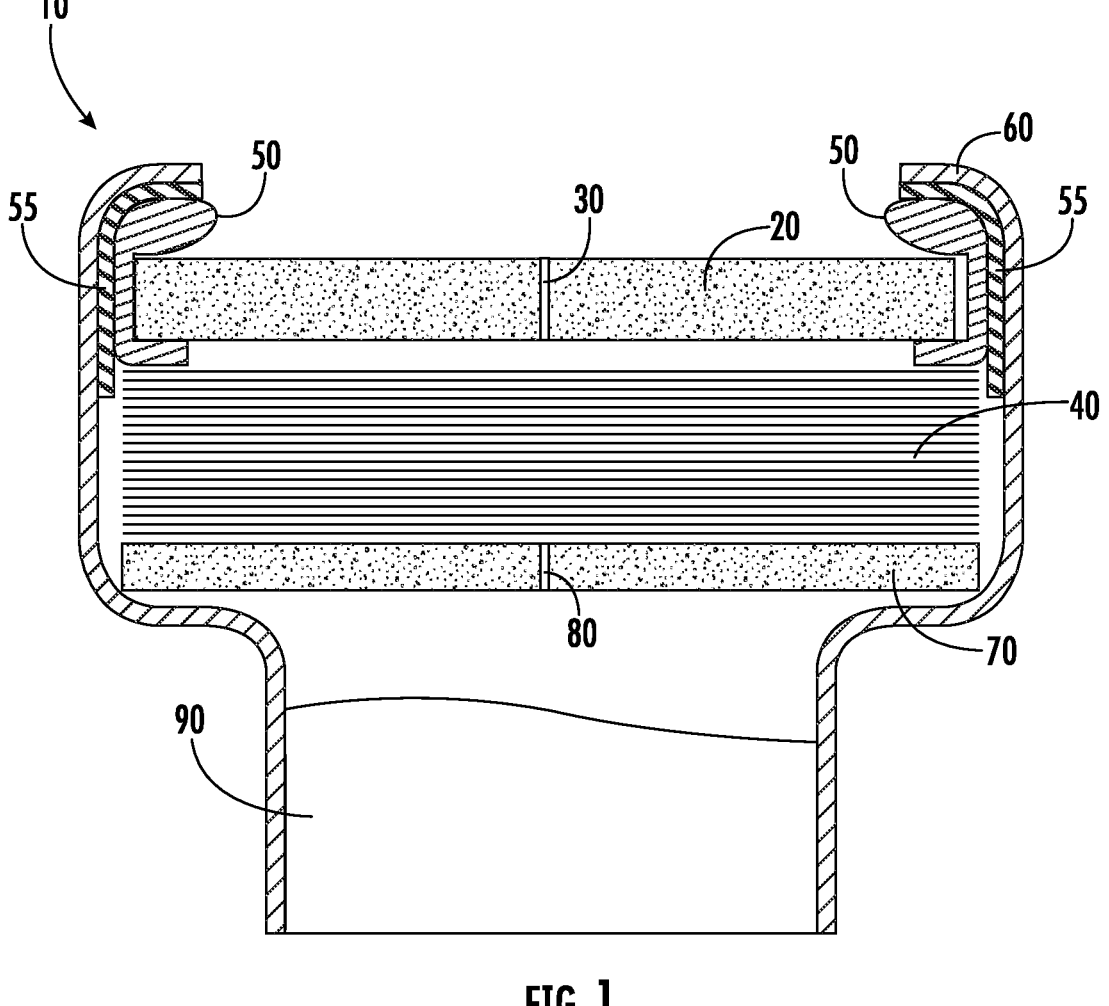
FIG. 1 is a schematic diagram of an embodiment of a gas detection device.

FIG. 1 shows a gas detection device 10 having a top disk 20, a first channel 30, an electrochemical sensor 40, a gasket 50, an electrically resistive material 55, a housing 60, a bottom disk 70, a second channel 80, and an optional reservoir 90.

The gas detection device 10 may be configured to detect carbon monoxide, volatile organic chemicals (VOCs), or explosive gasses such as ethane, propane, methane, hydrogen sulfide ($H_2S$), oxygen and hydrogen.

Figure 2:
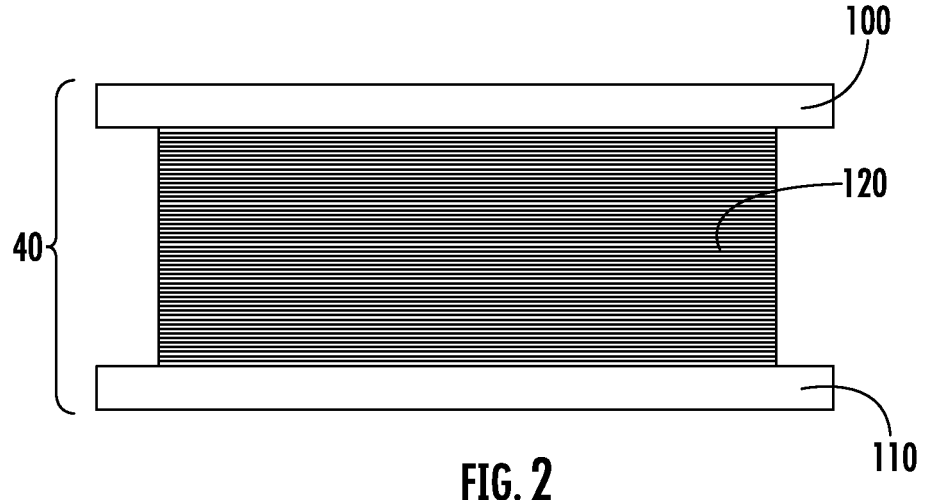
FIG. 2 is a schematic diagram of an electrochemical sensor with an MEA.

Housing 60 is electrically conductive. The electrochemical sensor 40 is operably coupled to housing 60. As shown in FIG. 2 the electrochemical sensor 40 is a membrane electrode assembly that includes a first electrode 100, a second electrode 110, and a membrane stack 120 located between the first electrode and the second electrode. The electrochemical sensor 40 may be located above an optional aqueous solution located in optional reservoir 90. The aqueous solution may be water, a concentrated salt solution (such as a concentrated salt solution of sodium chloride or lithium chloride) or an acid aqueous solution (such as a sulfuric acid solution). The second electrode is operably connected to housing 60 and located adjacent to reservoir 90.

The membrane stack is an assembled stack of polymer electrolyte membranes (PEM) or alkali anion exchange membranes (AAEM) that allows transport of the protons or hydroxide ions from the first electrode 100 to the second electrode 110 through the membrane stack 120 but forces the electrons to travel around a conductive path to the first electrode 100.

Figure 3:
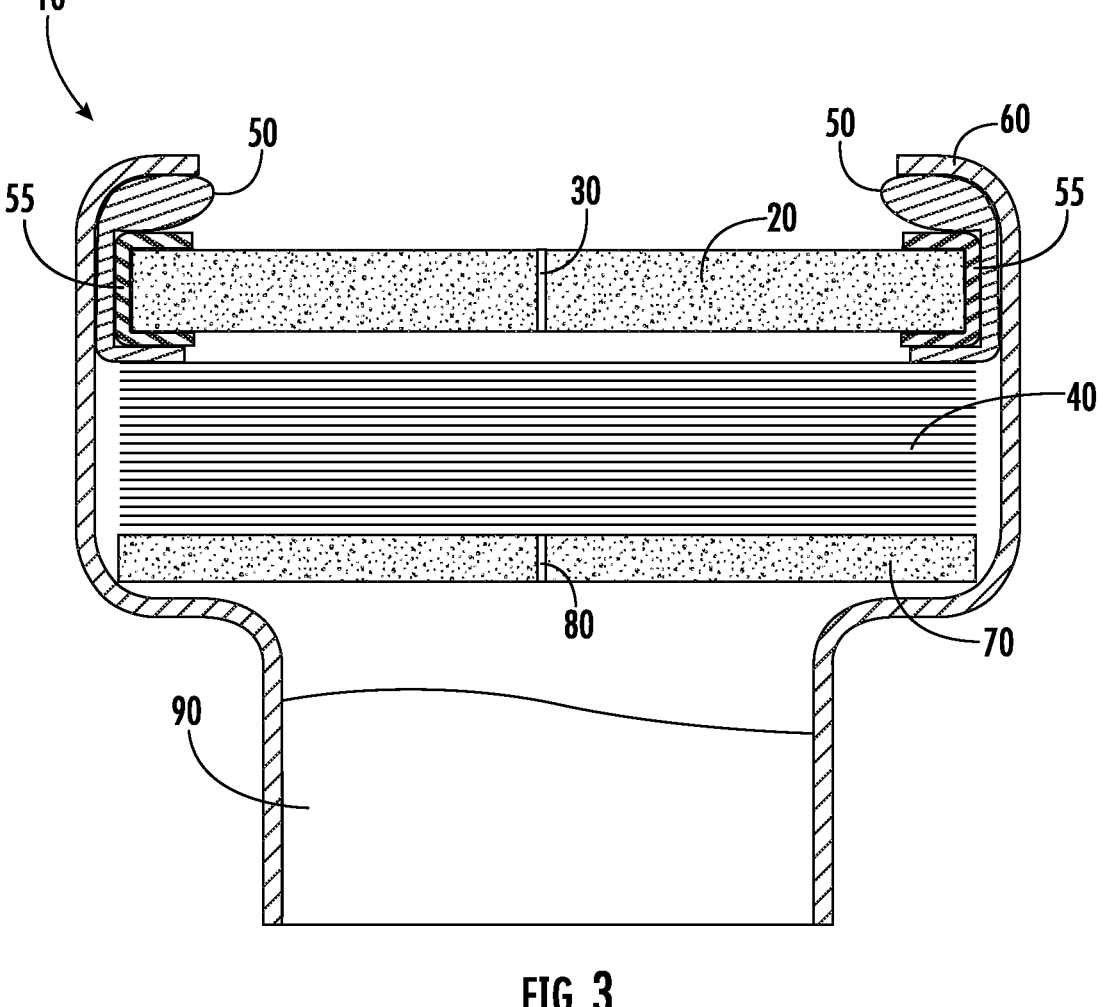
FIG. 3 is a schematic diagram of an embodiment of a gas detection device.

The electrically resistive material 55 prevents current bypass through the gasket by providing an additional layer of electrical insulation. The electrically resistive material 55 has a resistance greater than or equal to 100,000 ohms in certain instances. The electrically resistive material 55 may be formed or applied to the housing or to the gasket. It is also contemplated that the electrically resistive material 55 may be located between the gasket 50 and the top disk 20 as shown in FIG. 3. When the electrically resistive material 55 is formed or applied to the housing 60 or the top disk 20 the electrically resistive material 55 may be a paint, a film, an anodization coating, or the like. The electrically resistive material 55 may have a thickness of 2 to 5000 micrometers, or 10 to 1000 micrometers. When the electrically resistive material 55 is applied to the gasket 50 or top disk 20 the electrically resistive material 55 may be a paint or film and have a thickness of 10 to 5000 micrometers. The electrically resistive material 55 may be continuous so as to prevent current leakage through gaps in the material.

Figure 4A:
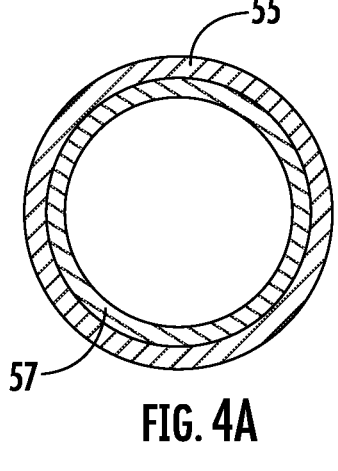
FIGS. 4A-C show embodiments of a composite gasket.
Figure 4B:
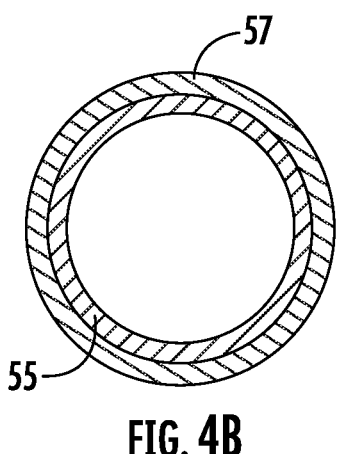
Figure 4C:
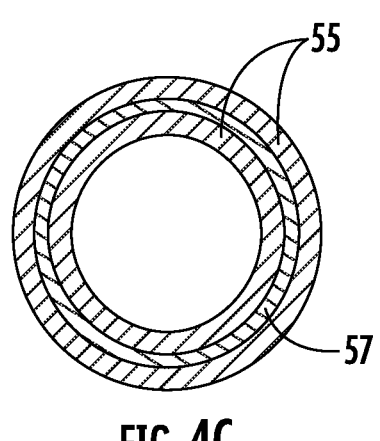

It is further contemplated that the electrically resistive material may be formed as part of the gasket 50 such that gasket 50 is a composite gasket which includes electrically resistive material different from the remainder of the gasket material. FIGS. 4A to 4C show different embodiments of a composite gasket. In FIG. 4A the electrically resistive material 55 is on an exterior surface that would contact the housing. In FIG. 4B the electrically resistive material 55 is on an exterior surface which faces the top disk. In FIG. 4C the electrically resistive material is on both exterior surfaces. In FIGS. 4A-4C, the second gasket material is indicated by 57. It is further contemplated that the electrically resistive material 55 may be dispersed in a material different from the electrically resistive material 55. The presence of islands of the electrically resistive material functions to inhibit conductive pathways that may develop in the material different from the electrically resistive material.

Exemplary composite gasket materials include silicone rubber, butyl rubber, fluorocarbon-based fluoroelastomer materials (also known as FKM or FPM), ethylene propylene diene monomer rubber (EPDM rubber), natural rubber and combinations thereof. Exemplary combinations of materials include silicone rubber/butyl rubber, silicone rubber/fluorocarbon-based fluoroelastomer and silicone rubber/EPDM rubber.

Use of the electrically resistive material 55 allows for a broader selection of materials to be used for the gasket.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof. Furthermore, the terms "comprises" and/or "comprising," as well as the terms "includes" and/or "including," support embodiments which do not incorporate elements other than those described.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A gas detection device comprising an electrically conductive housing, a top disk having a first channel, a bottom disk having a second channel, an electrochemical sensor disposed between the top disk and the bottom disk, a gasket separate from the electrochemical sensor, and an electrically resistive material;

wherein the top disk, bottom disk, electrochemical sensor, gasket and electrically resistive material are located in the housing and the electrically resistive material is located between the top disk and the gasket;

wherein the electrically resistive material is located between the top disk and the housing;

wherein the gasket is located between the top disk and the housing;

wherein the electrically resistive material is radially outward of the top disk;

wherein the gasket is radially outward of both the top disk and the electrically resistive material;

wherein the electrically resistive material is in contact with a top surface of the top disk, the electrically resistive material is in contact with an outer edge of the top disk, and the electrically resistive material is in contact with a bottom surface of the top disk.

2. The gas detection device of claim 1, wherein the electrochemical sensor comprises a membrane electrode assembly.

3. The gas detection device of claim 1, wherein the electrically resistive material is in contact with the gasket.

4. The gas detection device of claim 1, wherein the electrically resistive material has a thickness of 2 to 5000 micrometers.

5. The gas detection device of claim 1, wherein the electrically resistive material has a thickness of 10 to 1000 micrometers.

6. The gas detection device of claim 1, wherein the electrically resistive material has an electrical resistance greater than or equal to 100,000 ohms.

7. The gas detection device of claim 1, wherein the electrically resistive material comprises a paint, a film, or an anodization layer.

8. The gas detection device of claim 1, wherein the gasket is in contact with a top surface of the electrically resistive material, the gasket is in contact with an outer edge of the electrically resistive material, and the gasket is in contact with a bottom surface of the electrically resistive material.

* * * * *